(12) United States Patent
Neto et al.

(10) Patent No.: US 12,038,547 B2
(45) Date of Patent: Jul. 16, 2024

(54) ENTROPY-DIFFUSION METHOD FOR FRACTURE IDENTIFICATION AND LABELLING IN IMAGES

(71) Applicant: Halliburton Energy Services, Inc., Houston, TX (US)

(72) Inventors: Rafael March Castaneda Neto, Rio de Janeiro (BR); Naum Moiseyevic Derzhi, Houston, TX (US); Jonas Toelke, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 253 days.

(21) Appl. No.: 17/587,933

(22) Filed: Jan. 28, 2022

(65) Prior Publication Data

US 2023/0243993 A1    Aug. 3, 2023

(51) Int. Cl.
| | |
|---|---|
| G01V 1/50 | (2006.01) |
| G01N 23/046 | (2018.01) |
| G01N 33/24 | (2006.01) |
| G01V 1/46 | (2006.01) |
| G01V 20/00 | (2024.01) |
| G06T 7/44 | (2017.01) |
| G06V 10/40 | (2022.01) |
| G06V 20/69 | (2022.01) |
| A61B 5/00 | (2006.01) |

(52) U.S. Cl.
CPC ............ *G01V 1/50* (2013.01); *G01N 23/046* (2013.01); *G01N 33/24* (2013.01); *G01V 1/46* (2013.01);
(Continued)

(58) Field of Classification Search
None
See application file for complete search history.

(56) References Cited

U.S. PATENT DOCUMENTS

| | | | |
|---|---|---|---|
| 9,258,550 B1 * | 2/2016 | Sieracki | G06V 20/63 |
| 9,934,586 B2 * | 4/2018 | Yu | G06T 7/149 |

(Continued)

FOREIGN PATENT DOCUMENTS

KR    20150054084 A    5/2015

OTHER PUBLICATIONS

Lee, Detecting Micro Fractures With X-Ray Computed Tomography, arXiv.org, (Year: 2021).*

(Continued)

*Primary Examiner* — Isam A Alsomiri
*Assistant Examiner* — Vikas Atmakuri
(74) *Attorney, Agent, or Firm* — John Wustenberg; Parker Justiss, P.C.

(57) ABSTRACT

The disclosure provides an approach, or workflow, that extrapolates a segmentation carried out on a formation image into the labelling of fractures. The workflow can be applied to 2D and 3D images, which can be generated by different imaging technologies. Advantageously, one or more steps of the workflow can be performed automatically. An example of the workflow includes: (1) distinguishing fractures identified in a formation image from a background of the formation image by applying an entropy filter, wherein the formation image has elements that are defined as either fracture elements or non-fracture elements and entropy values for the elements are generated by the applying of the entropy filter, and (2) identifying the fracture elements that correspond to the fractures by solving a diffusion equation, wherein the entropy values are used as a diffusivity field for solving the diffusing equation and the fracture elements are used as a source.

20 Claims, 3 Drawing Sheets

(52) U.S. Cl.
CPC .............. *G01V 20/00* (2024.01); *G06T 7/44* (2017.01); *G06V 10/40* (2022.01); *G06V 20/698* (2022.01); *A61B 5/725* (2013.01); *G01N 2223/419* (2013.01); *G01V 2200/16* (2013.01); *G06T 2207/20024* (2013.01)

(56) References Cited

U.S. PATENT DOCUMENTS

| | | | | |
|---|---|---|---|---|
| 11,164,045 | B2* | 11/2021 | Paik | G06F 3/167 |
| 11,353,615 | B2* | 6/2022 | Assous | G01V 1/305 |
| 2006/0247525 | A1* | 11/2006 | Huo | G06T 7/0012 600/437 |
| 2010/0128933 | A1 | 5/2010 | Derzhi et al. | |
| 2015/0262417 | A1 | 9/2015 | Koroteev et al. | |
| 2016/0361043 | A1* | 12/2016 | Kim | A61B 8/0891 |
| 2018/0223641 | A1* | 8/2018 | Ciezobka | G01N 15/0227 |
| 2020/0190977 | A1 | 6/2020 | Kashikar et al. | |
| 2020/0333234 | A1 | 10/2020 | Al Marzouqi et al. | |
| 2022/0003891 | A1 | 1/2022 | Alkhaldi | |

OTHER PUBLICATIONS

Porsani, A combined Wigner-Ville and maximum entropy method for high-resolution time-frequency analysis of seismic data, Geophysics, December (Year: 2015).*

Ramandi, et al.; "Micro-CT image calibration to improve fracture aperture measurement"; Case Studies in Nondestructive Testing and Evaluation; Elsevier; 2016; 10 pgs.

* cited by examiner

ENTROPY-DIFFUSION METHOD FOR FRACTURE IDENTIFICATION AND LABELLING IN IMAGES

TECHNICAL FIELD

This disclosure relates to, in general, fractures in subterranean formations and, more specifically, to identifying and labelling fractures in subterranean formations.

BACKGROUND

Fractures can impact the petrophysical properties of subterranean formations and play an important role in subsurface fluid flow. For instance, fractures often increase the permeability of a subterranean formation by providing pathways for rapid fluid flow or by connecting rock pores. Identifying fractures in subterranean formations, therefore, can be beneficial in the pursuit of subterranean hydrocarbon reserves.

Identifying fractures in images of a subterranean formation can be difficult and usually requires a trained specialist. For instance, a trained specialist can pick different features of a radial image of a whole core of a subterranean formation using petrophysical software. Examples of the different features include fractures, sinusoidal shapes, or small cracks.

SUMMARY

In one aspect the disclosure provides a method for identifying and labelling fractures in formation images. In one example, the method includes: (1) applying an entropy filter to elements of a binary image and normalizing entropy values of the elements, wherein the binary image is from a formation image and has elements that are defined as either fracture elements or non-fracture elements, (2) generating a diffused image using the normalized entropy values of the elements as a diffusivity field in a diffusion equation solver and the fracture elements as source, (3) separating elements of the diffused image into a fracture class and a non-fracture class, (4) determining distinct fractures of the elements in the fracture class and assigning diffused image fracture labels to each fracture, and (5) labelling the fracture elements of the binary image located within the fractures of the diffused image with the diffused image fracture labels.

In another aspect, the disclosure provides a computing system for automated processing of formation images. In one example, the computing system includes one or more processors to perform one or more operations including: (1) distinguishing fractures identified in a formation image from a background of the formation image by applying an entropy filter, wherein the formation image has elements that are defined as either fracture elements or non-fracture elements and entropy values for the elements are generated by the applying of the entropy filter, and (2) identifying the fracture elements that correspond to the fractures by solving a diffusion equation, wherein the entropy values are used as a diffusivity field for solving the diffusing equation and the fracture elements are used as a source.

In yet another aspect, the disclosure provides a computer program product having a series of operating instructions stored on a non-transitory computer-readable medium that directs a computing system when executed thereby to perform operations to identify and label fractures from a binary image created from an image of a core sample of a formation. In one example the operations, include: (1) distinguishing fractures identified in the binary image from a background of the binary image by applying an entropy filter, wherein the binary image has elements that are defined as either fracture elements or non-fracture elements and entropy values for the elements are generated by the applying of the entropy filter, and (2) identifying the fracture elements that correspond to the fractures by solving a diffusion equation, wherein the entropy values are used as a diffusivity field for solving the diffusion equation and the fracture elements are used as a source.

BRIEF DESCRIPTION

Reference is now made to the following descriptions taken in conjunction with the accompanying drawings, in which.

DETAILED DESCRIPTION

Figure 1:
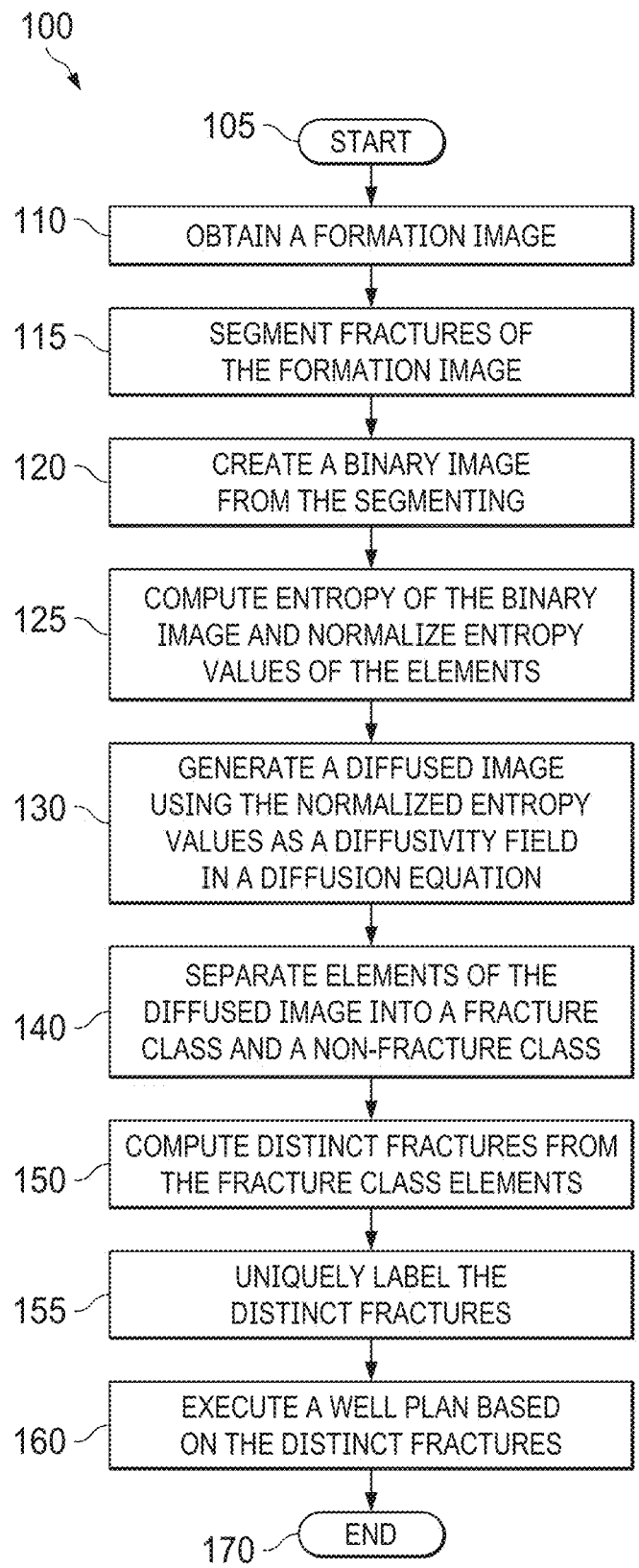
FIG. 1 illustrates a flow diagram of an example of a workflow for identifying and labelling fractures in formation images carried out according to the principles of the disclosure.

Fractures of the rock formation are heterogeneities, which have a low aspect ratio, defined here as ratio between the smallest dimension of the fracture to the largest one, in one direction. The fractures manifest in rock images as lines (2D images) or surfaces (3D images) of sharp contrast between image pixel values inside and outside of the fracture. Usually there are multiple fractures within one rock image, fracture walls are rough, fracture aperture and content may vary along the fracture, they are limited in extent and often are non-planar structures. As a result, the fracture image characteristics may change along the fracture, making its visual expression discontinuous. While it may be possible to identify which image pixels belong to fractures using segmentation based on voxel values, the task of separating segmented voxels belonging to fractures from segmented voxels belonging to other features (e.g., pores, high density nodules), assigning the segmented voxels to distinct fractures and tracing a particular fracture through its discontinuous image is challenging.

While a manual identification process can be used with 2D images, a manual-picking approach for fractures of 3D images of a subterranean formation is unfeasible due at least to the amount of time required to complete the task. For example, a user would have to operate on several slices of an image and some interpolation method would have to be used in order to connect the different fractures that are identified from 3D images.

Fractures exist at all spatial scales and identifying and labelling them can be important in petrophysical workflows, since the fractures often have a noticeable impact in the petrophysical properties of a formation, such as permeability, resistivity and elastic parameters. With improved fracture knowledge, more accurate well plans can be developed and executed to aid in the recovery of hydrocarbon resources. Accordingly, an improved approach for identifying fractures in formation images would be beneficial to the oil and gas industry.

The disclosure recognizes the above deficiencies and introduces a workflow to identify and label fractures in formation images, such as 2D and 3D images. The disclosed approach includes at least some automated steps that can enable or speed-up the identification of fractures from the images and provide insights on the fracture properties and the impact in petrophysical properties that the fractures provide. The formation images can originate from various types of imaging technologies. A non-limiting list of example imaging technologies include X-Ray CT scanners, Scanning Electron Microscopes (FIB-SEM), and Thin-Sections micrographs. As noted herein, the images can be from core samples of a formation, or borehole imaging.

The disclosed approach, or workflow, extrapolates a segmentation carried out on a formation image into the labelling of fractures. The workflow can be applied to 2D and 3D images. Advantageously, the disclosed approach can identify the 3D structure of the fractures from 3D images generated by different imaging technologies. 2D and 3D images are composed of discrete elements that are defined as pixels for 2D images and voxels for 3D images, wherein a pixel has x, y coordinates and a voxel has x, y, z coordinates in the respective images. Element or elements is used herein to collectively refer to the discrete elements of a 2D and 3D image. Fractures is used herein as an all-encompassing generic term to refer to fractures, cracks, veins or stylolites; i.e. any geological feature that has locally a low aspect ratio structure and is represented in the image by elements strongly differing by their values from the surrounding elements.

Figure 2:
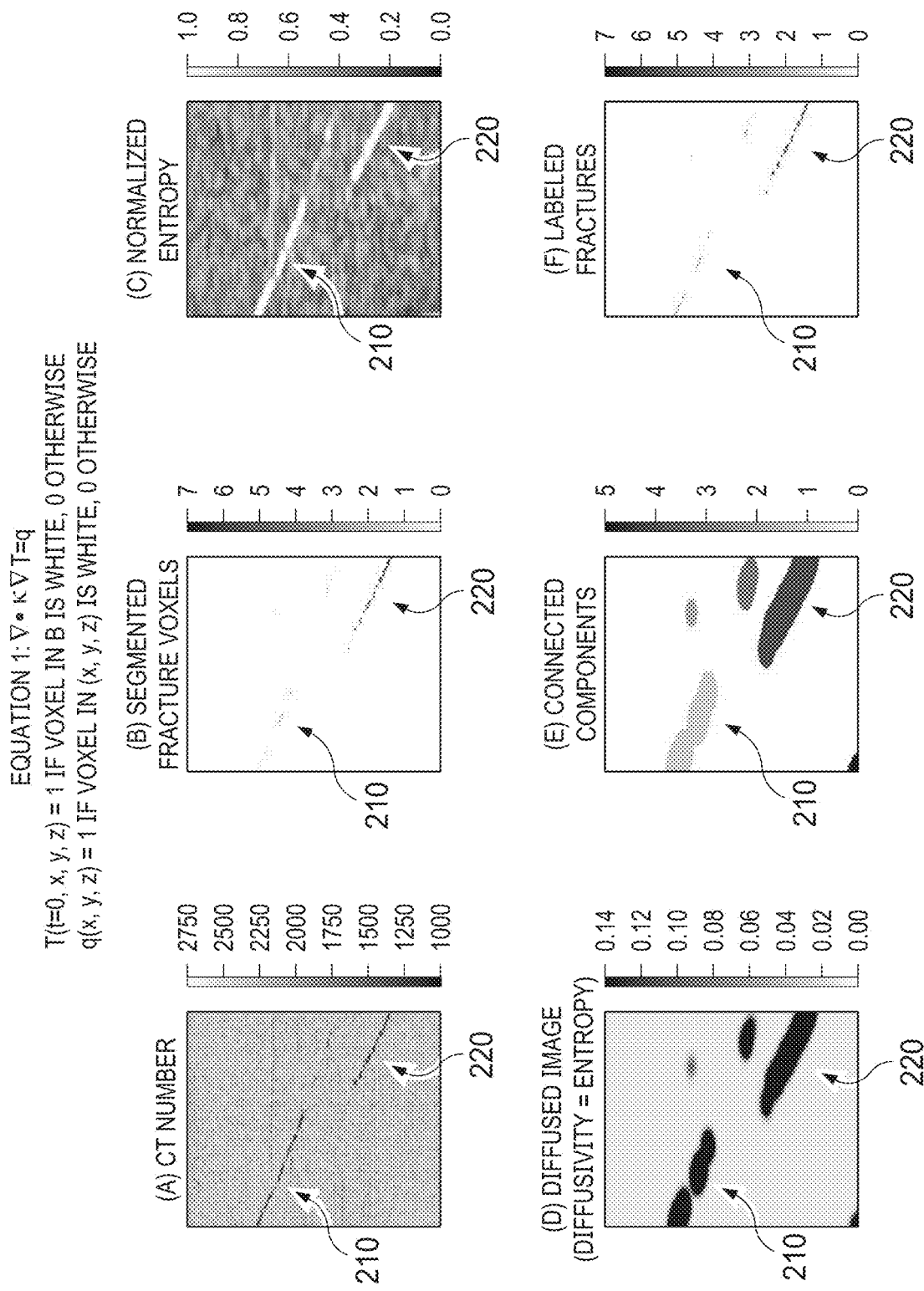
FIG. 2 illustrates a series of 2D images that provide a visual example of image processing according to the workflow 100 of FIG. 1.

FIG. 1 illustrates a flow diagram of an example of a workflow 100 for identifying and labelling fractures in formation images carried out according to the principles of the disclosure. The workflow 100 uses a combination of image filters, numerical simulation, and assisted segmentation for the identification and labelling. Various steps of the workflow 100 can be automatically performed. A computing device can perform the automated steps according to algorithms that correspond to the steps of the workflow 100. The algorithms can be represented as a series of operating instructions that direct the operation of one or more processors of the computing device when executed thereby. The workflow 100 can be applied to, for example, 2D and 3D images. FIG. 2 includes a series of 2D images that provide a visual example of image processing according to the workflow 100 and will be referred to throughout the below description. The progression of identifying and labelling of two different fractures, fracture 210 and 220, are noted in the different images of FIG. 2. The workflow 100 begins in step 105.

In step 110, a formation image is obtained. The formation image is from a subterranean formation and can be generated via various imaging technologies. The formation image can be from a core sample that was collected from the formation. Accordingly, the formation image can be obtained from a lab using one or more different imaging technologies. For example, X-Ray CT scanners, Scanning Electron Microscopes (FIB-SEM), Thin-Sections can be used. Image A in FIG. 2 illustrates an example of a formation image obtained from a CT scan a core sample. However, the procedure is general and may be applied to images originated from other sources such as acoustic or resistive borehole image logs.

In step 115, voxels corresponding to fractures of the formation image are segmented. These voxels can be isolated pores belonging to a fracture. Segmenting of the voxels assists in distinguishing fractures from other formation features. Elements of a formation image typically represent a range of values instead of simply each element being one of two different ones. For example, the elements in image A of FIG. 2 have a value within a range of values. Segmenting typically includes determining a series of value ranges for fracture elements of the formation image to classify each element as a fracture element or a non-fracture element.

Segmenting is beneficial since a fracture is not always shown to be completely open in a formation image. For example, a portion of a fracture can be filled with minerals. Additionally, fracture elements of a formation image that are within a fracture may not be necessarily connected due to sub-resolution apertures within the fracture that lead to some fracture elements' values lying outside of a fracture value range.

A trained specialist, such as a trained geologist, can perform the segmenting of fractures. A computer program can also be used for automated segmenting. The determined value range can be applied to the whole 3D formation image.

In step 120, a segmented image is created as a result of the segmentation procedure. The image is a segmentation output where fracture elements are labeled differently than non-fracture elements. Image B of FIG. 2 illustrates an example of an image created from segmenting of formation image A. The grayscale color bar of image B is integer numbers that correspond to different colors for different labels of distinct fractures.

An entropy of the original image is computed in step 125. After the segmentation and creation of the binary image, an entropy filter is used to automatically identify the structure of the fractures. Image C of FIG. 2 illustrates the benefits of computing the entropy values of the binary image elements to aid in the identification of fractures 210 and 220. Essentially, the entropy value of each element measures the "strangeness" of the element value distribution within a small region surrounding the element. For example, if contiguous elements have the same color value, the entropy value between the contiguous elements would be zero, such as with the elements of the background formation. However, since a fracture is typically a sharp edge, entropy tends to increase in the fracture planes. The entropy values assist in further distinguishing fracture elements from the background, i.e., non-fracture elements, regardless the color values that are used. After application of the entropy filter to the binary image, the entropy values of the image elements are typically normalized as represented in image C of FIG. 2. A benefit of the entropy filter is that it captures the "strangeness" in fractures even if the fracture aperture is below the image resolution or the fracture is locally filled with high-density material.

In step 130, a diffused image is generated using the normalized entropy values as a diffusivity field in a diffusion equation. The entropy values for the elements provide the magnitude of the diffusivity and the segmented fracture elements provide the elements to be used as heat source for the solution of a diffusion equation that connects the fracture elements. The diffusion equation is the divergence of the diffusivity tensor times a gradient field that is referred to as the temperature. Different diffusion equations can be used and solved, wherein the solution is the temperature that corresponds to each element of the image. A diffusion equation solver, therefore, is used to determine the temperature for each element. Equation 1 shown in FIG. 2 is an example of a diffusion equation that can be used.

In Equation 1, K are the entropy values of the elements generated by the application of the entropy filter and are used to indicate a diffusivity field for the diffusion equation.

q is the initial condition or heat source that can be assigned. An initial temperature can be assigned to each element that is a fracture and another initial temperature can be assigned to each element that is not a fracture. The temperature assigned to the fracture elements can be higher than the temperature assigned to the non-fracture elements. As the diffusion equation runs, the higher temperature spreads (diffuses) and more clearly defines the fractures as illustrated in image D of FIG. 2. The fractures are similarly represented in image D as in the previous images A to C but with a larger region due to the diffusion.

Regardless the diffusion equation that is used, the parameters need to be tuned. Temperature levels, diffusion time, etc. are examples of parameters to set for operating the diffusion equation. The parameters values can be established based on, for example, empirical data. Values can be estimated based on, for instance, a typical length scale of fracture apertures or other empirical data. The run time can be set, for example, based on the number of fractures. A geologist or other trained professionals can provide input on setting the parameters. Machine learning can also be used to determine parameter values based on training from empirical data. Machine learning may also be used to help in distinguishing fractures in homogenous images.

After a few transient iterations of the diffusion equation, the fracture elements of different fractures, such as fracture 210 and fracture 220, can be identified and are ready to be labelled accordingly. This approach works best for identification of non-connected small cracks, which is exactly when traditional techniques fail to provide reasonable information on fracture structures.

In step 140, elements of the diffused image are separated into a fracture class or a non-fracture class. Essentially a binary image is generated from the diffused image. A threshold can be applied for segmentation to create this binary image. In image D of FIG. 2, the diffused image includes elements that are black and elements that are non-black, wherein the black elements correspond to fractures. All of the non-black elements can be set to the same class and represented by the same color. As such, another image is created, image E, having elements that are either fracture elements or non-fracture elements. However, due to entropy filtering and diffusion, the area of the fractures is larger in image E compared to the fracture areas in image B.

In step 150, distinct fractures are computed from the fracture class elements. Distinct neighborhoods of fracture elements can be identified using standard image processing techniques. These techniques are typically called "connected components labeling algorithms" and are well established and available in image processing libraries. Accordingly, the fracture elements of the different fractures can be grouped together resulting in different fractures that are not connected. The result of this algorithm is shown in image E as we see the different fracture regions labelled differently and shown with different colors.

In step 155, the distinct fractures are uniquely labeled. Each of the distinct fractures can be labeled a different color. As such, the different fractures can be visually identified for easier manual analysis. Image F illustrates an example of an output image having different labelled fractures. The output image can be provided to a screen of a computing device for visual analysis. A geologist or another trained professional can review the uniquely labeled fractures and determine an action based thereon. The output image can be provided to reservoir simulators for subsequent analysis (visual or actual).

In step 160, a well plan is executed based on the distinct fractures. The well plan can involve, for example, determining wellbore locations, selecting well equipment, controlling production, etc. The workflow 100 can be performed after drilling a well and a well plan based thereon may be used to control production after completion. The workflow 100 can also be used before completion to determine if a well sight would be profitable for recovery. As such, the well plan may include leaving a well sight. The well plan can be executed for future wells having a similar formation, such as a proximate well sight. The workflow 100 ends in step 170.

FIG. 2 illustrates various views of an example of a 2D slice of a 3D scanned image of a formation core sample representing the identification and labelling of fractures according to the principles of the disclosure. The process demonstrated in FIG. 2 can equally apply to a 3D image. The disclosed process separates the fractures from the background image of the formation, which is a core sample in FIG. 2. The core sample can be obtained via conventional procedures used in the industry. The core sample can be, for example, a cylinder of four to six meters in length.

The series of views in FIG. 2 starts with image A, which illustrates the 2D slice of the 3D image. In this example, the 3D image is obtained via a CT scan of the core sample. As noted herein, the process demonstrated in FIG. 2 also applies to images that are created via other technologies. Image A illustrates fractures in the core sample, such as fractures 210 and 220. The fractures can have perturbations and are not necessarily planar but can have curvature, such as in both fractures 210 and 220. Additionally, image (A) is in grayscale wherein elements are not simply black or white. As such, elements cannot simply be separated and labelled as non-fractures and fractures in image A. Furthermore, the fractures may not be fully open but can be filled with a material in some areas. For example, fracture 210 includes black elements that indicate empty space and white space that indicates minerals.

The grayscale color bar of image A represents standard CT numbers, wherein different CT numbers correspond to different colors on a gray scale. For example, the spaces have no density and are represented by black and the minerals that have density are represented by white. Different CT values levels of the formation grain and pores are also evident in image A. Some pores may be under the resolution of the image and therefore not visible in image A.

The image scale can vary depending on the imaging technology that is used to capture the formation properties. RF signals is an example of another technology that can be used to capture formation properties. The RF signals can be used to distinguish between fractures and non-fractures in radial images where planar fractures can be represented as sinusoidal signals.

Image B is a binary image wherein each of the elements is identified as a fracture element or a non-fracture element. As noted in the above discussion of steps 115 and 120 of workflow 100, image B is a result of segmenting image A. The grayscale color bar of image B is integer numbers that correspond to different colors for different labels of distinct fractures.

Image C is after an entropy filter has been applied to the original image A. As noted above with respect to step 125, the entropy values of the elements represent the "strangeness" compared to surrounding elements and assist in further distinguishing fracture elements from the background, i.e., non-fracture elements. After application of the entropy filter to the binary image, the entropy values of the image elements are typically normalized as represented by the grayscale color bar of image C.

Image D is a diffused image generated from image C using a diffusion equation. The normalized entropy values are used as a diffusivity field in a diffusion equation solver that has as initial state the field of the fracture segmented elements. Step 130 of workflow 100 can be used to generate image D.

Image D is essentially a resulting image of a transient evolution of a temperature field. For example, some elements can be identified as hot, i.e., belonging to a fracture, and some elements can be identified as cold, i.e., belonging to the background rock of the formation. Then, as time goes by, the temperature of the hot elements diffuses heating up the cold elements; preferentially in the direction of the fracture plane. Via diffusion, the temperature field is diffused, connecting the fracture elements, such as shown with respect to fractures 210 and 220. The grayscale color bar of image D represents particular colors that are used to distinguish between the background and fracture components.

Image E is a binary image resulting from the application of a threshold segmentation to diffused image D. Image E includes elements separated into two classes, with one class representing fracture elements and another class representing non-fracture elements. The grayscale color bar of image E is integer numbers that correspond to different colors for different labels of distinct fractures, wherein connected components will assign an integer label to each voxel.

Image F is an output image representing the identification and labelling for fractures from a formation image via an entropy-diffusion method disclosed herein. Image F corresponds to step 155 of the workflow 100, wherein distinct fractures are identified and labeled. In image F, fracture 210 is identified separately from fracture 220 by different labels (shown with distinct colors). The grayscale color bar of image F is integer numbers that correspond to different colors for different labels of distinct fractures.

Figure 3:
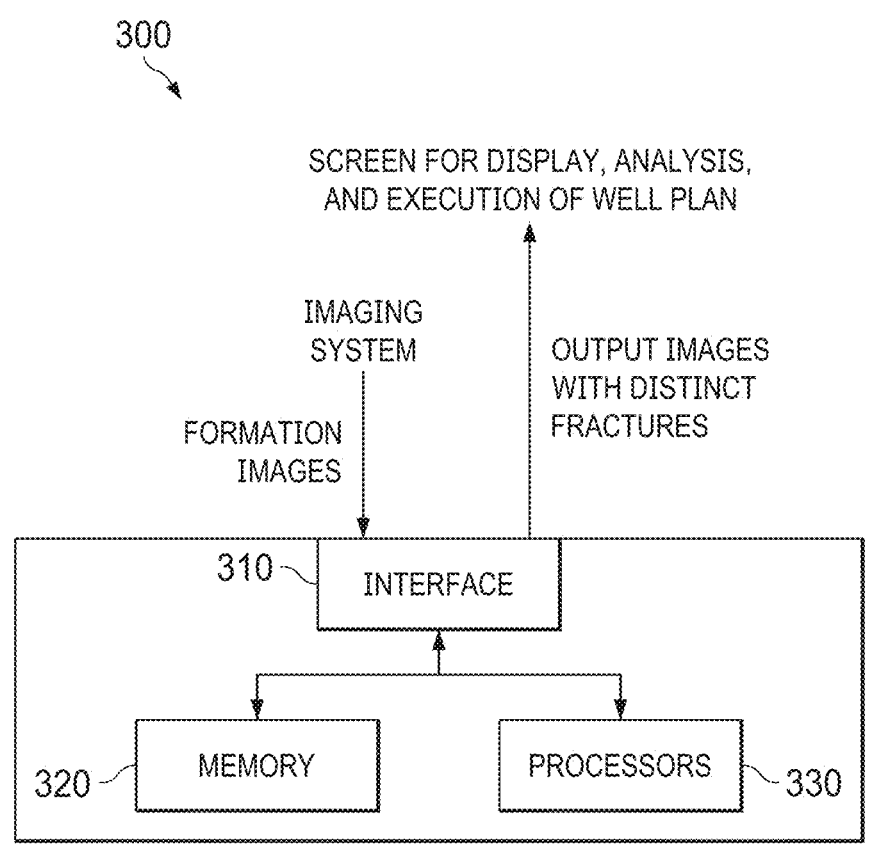
FIG. 3 illustrates a block diagram of an example of a computing system that identifies and labels fractures from formation images according to the principles of the disclosure.

FIG. 3 illustrates a block diagram of an example of a computing system 300 that identifies and labels fractures from formation images according to the principles of the disclosure. The computing system 300 is typically implemented on one or more computing devices that can be at a well site or distant, such as in a cloud environment, a data center, a lab, or a corporate office. The computing system 300 can be a laptop, smartphone, personal digital assistant (PDA), server, desktop computer, cloud computing system, other computing systems, or a combination thereof, which is operable to perform the processes and methods described herein, such as one or more of the steps of workflow 100. Well site planners, engineers, and other personnel can send or input data and instruction to the computing system 300, such as parameter inputs, and receive data from the computing system 300, such as output diagrams of uniquely labeled fractures, and other information by various conventional.

The computing system 300 is configured to process formation images to identify and label fractures thereof using an entropy-diffusion method or workflow as disclosed herein. For example, the computing system 300 can also automatically perform at least some of the steps of workflow 100. The computing system 300 includes an interface 310, a memory 320, and one or more processors 330.

The interface 310 is configured to receive and transmit data. As such, the interface 310 includes the necessary circuitry, software, logic, for communicating data. The interface 310 can receive formation images for processing. The formation images can be binary images derived from an image of a core sample. Output images can also be sent from the processor 330 or memory 320 via the interface 310 to a screen for display and analysis. The screen can be part of the computing system 300.

The memory 320 is configured to store the formation images and operating instructions that direct operation of the one or more processors 330. The operating instructions can correspond to various ones of the automated steps of the workflow 100. The memory 320 can also store parameters for a diffusion equation that is used for processing the formation images. A trained machine learning model can also be stored on the memory 320 that is used in selecting or modifying the parameters for the diffusion equation.

The one or more processors 330 are configured to process formation images using an entropy-diffusion combination as disclosed herein. The one or more processors 330 can be configured to operate according to one or more algorithms corresponding to at least some of the steps of the workflow 100. For example, the one or processor 330 can be configured to distinguish fractures identified in a formation image from a background of the formation image by applying an entropy filter. The formation image can be a binary image that has elements defined as either fracture elements or non-fracture elements and entropy values for the elements are generated by applying the entropy filter. Additionally, the one or more processors 330 can identify the fracture elements that correspond to the fractures by solving a diffusion equation, wherein the entropy values are used as a diffusivity field for solving the diffusing equation and fracture elements are used as sources.

A portion of the above-described apparatus, systems or methods may be embodied in or performed by various analog or digital data processors, wherein the processors are programmed or store executable programs of sequences of software instructions to perform one or more of the steps of the methods. A processor may be, for example, a programmable logic device such as a programmable array logic (PAL), a generic array logic (GAL), a field programmable gate arrays (FPGA), or another type of computer processing device (CPD). The software instructions of such programs may represent algorithms and be encoded in machine-executable form on non-transitory digital data storage media, e.g., magnetic or optical disks, random-access memory (RAM), magnetic hard disks, flash memories, and/or read-only memory (ROM), to enable various types of digital data processors or computers to perform one, multiple or all of the steps of one or more of the above-described methods, or functions, systems or apparatuses described herein.

Portions of disclosed examples or embodiments may relate to computer storage products with a non-transitory computer-readable medium that have program code thereon for performing various computer-implemented operations that embody a part of an apparatus, device or carry out the steps of a method set forth herein. Non-transitory used herein refers to all computer-readable media except for transitory, propagating signals. Examples of non-transitory computer-readable media include, but are not limited to: magnetic media such as hard disks, floppy disks, and magnetic tape; optical media such as CD-ROM disks; magneto-optical media such as floppy disks; and hardware devices that are specially configured to store and execute program code, such as ROM and RAM devices. Examples of program code include both machine code, such as produced by a compiler, and files containing higher level code that may be executed by the computer using an interpreter.

In interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Those skilled in the art to which this application relates will appreciate that other and further additions, deletions, substitutions and modifications may be made to the described embodiments. It is also to be understood that the terminology used herein is for the purpose of describing particular embodiments only, and is not intended to be limiting, because the scope of the present disclosure will be limited only by the claims. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, a limited number of the exemplary methods and materials are described herein.

Aspects disclosed herein include:

A. A method for identifying and labelling fractures in formation images, including: (1) applying an entropy filter to elements of a binary image and normalizing entropy values of the elements, wherein the binary image is from a formation image and has elements that are defined as either fracture elements or non-fracture elements, (2) generating a diffused image using the normalized entropy values of the elements as a diffusivity field in a diffusion equation solver and the fracture elements as source, (3) separating elements of the diffused image into a fracture class and a non-fracture class, (4) determining distinct fractures of the elements in the fracture class and assigning diffused image fracture labels to each fracture, and (5) labelling the fracture elements of the binary image located within the fractures of the diffused image with the diffused image fracture labels.

B. A computing system for automated processing of formation images, comprising one or more processors to perform one or more operations including: (1) distinguishing fractures identified in a formation image from a background of the formation image by applying an entropy filter, wherein the formation image has elements that are defined as either fracture elements or non-fracture elements and entropy values for the elements are generated by the applying of the entropy filter, and (2) identifying the fracture elements that correspond to the fractures by solving a diffusion equation, wherein the entropy values are used as a diffusivity field for solving the diffusing equation and the fracture elements are used as a source.

C. A computer program product having a series of operating instructions stored on a non-transitory computer-readable medium that directs a computing system when executed thereby to perform operations to identify and label fractures from a binary image created from an image of a core sample of a formation, the operations, including: (1) distinguishing fractures identified in the binary image from a background of the binary image by applying an entropy filter, wherein the binary image has elements that are defined as either fracture elements or non-fracture elements and entropy values for the elements are generated by the applying of the entropy filter, and (2) identifying the fracture elements that correspond to the fractures by solving a diffusion equation, wherein the entropy values are used as a diffusivity field for solving the diffusion equation and the fracture elements are used as a source.

Each of aspects A, B, and C can have one or more of the following additional elements in combination. Element 1: wherein one or more of the applying, generating, separating, determining, or labelling are performed automatically. Element 2: further comprising segmenting fractures of the formation image, wherein the fracture elements and the non-fracture elements are defined based on the fracture element values. Element 3 wherein the segmenting is performed manually. Element 4: further comprising executing a well plan based on the labeled fracture elements. Element 5: wherein the formation image is a three-dimensional image. Element 6: wherein the formation image is from a core sample of the formation. Element 7: wherein the formation image is an image from a CT scan of the core sample. Element 8: wherein the generating a diffused image includes solving a diffusion equation for a temperature value for each of the fracture elements. Element 9: wherein the formation image is a binary image. Element 10: wherein the entropy values are normalized entropy values. Element 11: wherein the one or more operations further include determining distinct ones of the fractures and ones of the fracture elements that correspond to each of the distinct ones of the fractures. Element 12: wherein the one or more operations further include uniquely labeling each of the distinct ones of the fractures. Element 13: wherein the one or more operations further include generating an output image that includes the uniquely labeled distinct ones of the fractures and displaying the output image. Element 14: wherein the formation image is a binary image determined from a 3D image of a core sample of a formation. Element 15: wherein the formation image is a binary image determined from a CT scan of a core sample of a formation. Element 16: further comprising an interface that receives the formation image and a memory that stores the operating instructions for the one or more operations and stores the formation image. Element 17: wherein the operations further include separating elements of the diffused image into a fracture class and a non-fracture class, determining distinct fractures of the elements in the fracture class and assigning diffused image labels to each fracture, and labelling the fracture elements of the binary image located within the fractures of the diffused image with the diffused image fracture labels.

What is claimed is:

1. A method for identifying and labelling fractures in formation images, comprising:
   obtaining a binary image from a formation image, wherein the binary image has elements that are defined as either fracture elements or non-fracture elements;
   connecting the fracture elements using a processor generated a diffused image;
   determining distinct fractures in the diffused image using a processor and the connected fracture elements and assigning diffused image fracture labels to each fracture of the distinct fractures; and
   labelling the fracture elements of the binary image located within the fractures of the diffused image with the diffused image fracture labels.

2. The method as recited in claim 1, wherein one or more of the applying, generating, separating, determining, or labelling are performed automatically.

3. The method as recited in claim 1, further comprising segmenting fractures of the formation image, wherein the fracture elements and the non-fracture elements are defined based on the fracture element values.

4. The method as recited in claim 3, wherein the segmenting is performed manually.

5. The method as recited in claim 1, further comprising executing a well plan based on the labeled fracture elements.

6. The method as recited in claim 1, wherein the formation image is a three-dimensional image.

7. The method as recited in claim 1, wherein the formation image is from a core sample of the formation.

8. The method as recited in claim 7, wherein the formation image is an image from a CT scan of the core sample.

9. The method as recited in claim 1, wherein the diffused image is generated by a processor solving a diffusion equation for a temperature value for each of the fracture elements.

10. A computing system for automated processing of formation images, comprising:
   one or more processors to perform one or more operations including:
      obtaining a binary image from a formation image, wherein the binary image has elements that are defined as either fracture elements or non-fracture elements;
      connecting the fracture elements of the binary image using a diffused image;
      identifying distinct fractures in the diffused image from the connected fracture elements; and
      labelling the fracture elements of the binary image using the distinct fractures in the diffused image.

11. The computing system as recited in claim 10, wherein the fracture elements or non-fracture elements are defined using entropy values binary image.

12. The computing system as recited in claim 11, wherein the entropy values are normalized entropy values.

13. The computing system as recited in claim 11, wherein the one or more operations further include generating the entropy values by applying an entropy filter to the formation image.

14. The computing system as recited in claim 13, wherein the labeling includes labelling the fracture elements of the binary image based on the fracture elements that are located within the distinct fractures of the diffused image.

15. The computing system as recited in claim 14, wherein the one or more operations further include generating an output image that includes the labeled fracture elements of the binary image and displaying the output image.

16. The computing system as recited in claim 10, wherein the formation image is determined from a 3D image of a core sample of a formation.

17. The computing system as recited in claim 10, wherein the formation image is determined from a CT scan of a core sample of a formation.

18. The computing system as recited in claim 10, further comprising an interface that receives the formation image, and a memory that stores operating instructions for the one or more operations and stores the formation image.

19. A computer program product having a series of operating instructions stored on a non-transitory computer-readable medium that directs a computing system when executed thereby to perform operations to identify and label fractures from a binary image created from an image of a core sample of a formation, the operations, comprising:
   obtaining a binary image from, wherein the binary image has elements that are defined as either fracture elements or non-fracture elements;
   connecting the fracture elements of the binary image using a processor generated diffused image;
   identifying distinct fractures in the diffused image from the connected fracture elements; and
   labelling the fracture elements of the binary image using the distinct fractures in the diffused image.

20. The computer program product as recited in claim 19, wherein the labelling includes labelling the fracture elements of the binary image based on the fracture elements that are located within the distinct fractures of the diffused image.

* * * * *